United States Patent

Sano et al.

[11] Patent Number: 5,347,012
[45] Date of Patent: Sep. 13, 1994

[54] NAPHTHOTHIOPYRANONE DERIVATIVES

[75] Inventors: Tatsuhiko Sano, Omiya; Keiko Saijo, Saitama; Sadakazu Yokomori, Urawa; Yoshimoto Nakashima, Ageo; Katsuo Hatayama, Omiya, all of Japan

[73] Assignee: Taisho Pharmaceutical Co., Ltd., Tokyo, Japan

[21] Appl. No.: 952,544
[22] PCT Filed: Jun. 20, 1991
[86] PCT No.: PCT/JP91/00825
 § 371 Date: Dec. 11, 1992
 § 102(e) Date: Dec. 11, 1992
[87] PCT Pub. No.: WO92/00294
 PCT Pub. Date: Jan. 9, 1992

[30] Foreign Application Priority Data

Jun. 22, 1990 [JP] Japan .................. 2-164658

[51] Int. Cl.$^5$ .................. C07D 409/06
[52] U.S. Cl. .................. 548/311.4
[58] Field of Search .................. 548/311.4

[56] References Cited

U.S. PATENT DOCUMENTS 5,006,544 4/1991 North et al. .................. 548/311.4

FOREIGN PATENT DOCUMENTS 0363789 4/1990 European Pat. Off. .
0364274 4/1990 European Pat. Off. .

OTHER PUBLICATIONS

Chemical Abstracts, vol. 94, No. 7, abstract no. 47079p, (J. Org. Chem., 45(23), 4611-15 1980.
Chemical Abstracts, vol. 93, No.23, abstract no. 220537r, (Bull. Chem. Soc., Japan. 53(7), 2046-9 1980.

Primary Examiner—Patricia L. Morris
Attorney, Agent, or Firm—Oblon, Spivak, McClelland, Maier & Neustadt

[57] ABSTRACT

A naphthothiopyranone derivative represented by the formula:

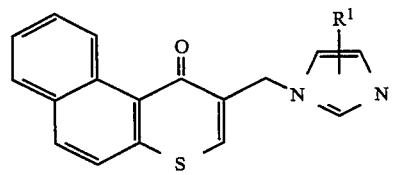

(wherein $R^1$ is a hydrogen atom or an alkyl group having 1 to 4 carbon atoms) and an acid addition salt thereof have more excellent antagonist effect at serotonin 3 receptors than the prior art compounds and the effects based thereon, e.g. anti-vomiting effect, gastrointestinal movement regulating effect and anti-anxiety effect.

18 Claims, No Drawings

NAPHTHOTHIOPYRANONE DERIVATIVES

DESCRIPTION

1. Technical Field

The present invention relates to naphthothiopyranone derivatives, and more particularly relates to naphthothiopyranone derivatives having the antagonist effect of 5-HT (serotonin) at 5-$HT_3$ (serotonin 3) receptors.

Background Art

Compounds described in EP-A-364274 have heretofore been known as having the structure and effect similar to those of the compounds of the present invention, but they do not have a satisfactory degree of the drug effect.

An object of the present invention is to provide compounds having more excellent anti-vomiting effect, gastrointestinal movement regulating effect and antianxiety effect based on the antagonist effect at serotonin 3 receptors than the prior art compounds.

DISCLOSURE OF THE INVENTION

The present invention is a naphthothiopyranone derivative represented by the formula:

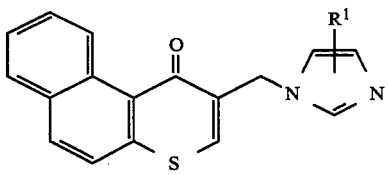

(wherein $R^1$ is a hydrogen atom or an alkyl group having 1 to 4 carbon atoms) or an acid addition salt thereof, and further a compound represented by the formula:

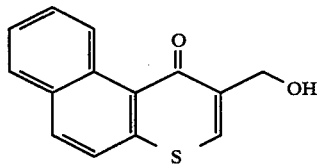

which is an intermediate of the compound of Formula (I).

In the present invention, the alkyl group having 1 to 4 carbon atoms means a straight or branched chain alkyl group. The acid addition salt of the compound of Formula (I) means an addition salt of a pharmacologically acceptable acid, for example, hydrochloride, hydrobromide, hydroiodide, sulfate, acetate, citrate, maloate, maleate, tartarate and succinate.

The compound of Formula (I) of the present invention can be prepared, for example, by the following processes.

A compound of Formula (II) is first reacted with a halogenating agent of common use (e.g. hydrobromic acid, thionyl chloride, phosphorus pentachloride, thionyl bromide and phosphorus tribromide) in an organic solvent or without solvent to give a compound represented by the formula:

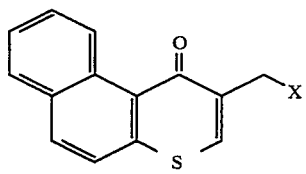

(wherein X is a halogen atom). The halogen atom herein means a chlorine atom, a bromine atom or an iodine atom. Examples of the organic solvent to be used are tetrahydrofuran, dioxane, ether, benzene, toluene, chloroform, dichloromethane, carbon tetrachloride, pyridine and a mixture of these solvents with hexamethylphosphorus triamide. A base such as triethylamine can also be added.

The compound obtained above is reacted with a compound represented by the formula:

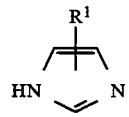

(wherein $R^1$ is as defined above) or an acid addition salt thereof in an organic solvent in the presence or absence of a base to give a compound of Formula (I). Examples of the base to be used in the reaction are triethylamine, pyridine, potassium carbonate, sodium carbonate, lithium carbonate, cesium carbonate, sodium bicarbonate, sodiumshydride, sodium hydroxide, potassium hydroxide, sodium ethoxide and potassium t-butoxide ("base" used hereinafter in the term of the disclosure of the invention is the same as defined herein). Examples of the organic solvent to be used are dichloromethane, chloroform, carbon tetrachloride, tetrahydrofuran, diethyl ether, dioxane, N,N-dimethylformamide, benzene, toluene and alcohols. In addition, iodides (e.g. potassium iodide) or phase-transfer catalysts (e.g. tetrabutylammonium bromide) can be used as a catalyst to accelerate the reaction.

On the other hand, the compound of Formula (II) of the intermediate is a novel compound and can be prepared, for example, by the following processes.

A known compound represented by the formula:

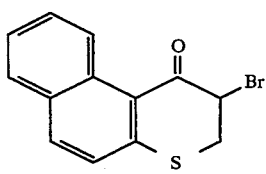

which can be prepared by the method described in Journal of Chemical Society, Parkin Trans. I, vol. 6, pp. 787–792 (1972), is reacted with formaldehyde in the presence of a base in an organic solvent at from room temperature to the boiling point of the solvent to give the compound of Formula (II). Examples of the organic solvent to be used in the reaction are tetrahydrofuran, dioxane, methanol, ethanol, isopropanol and N,N-dimethylformamide.

On the other hand, the compound of Formula (III) is reacted with formamide in the presence of a base in an organic solvent at from a temperature under ice-cooling to room temperature, and then the resulting compound represented by the formula:

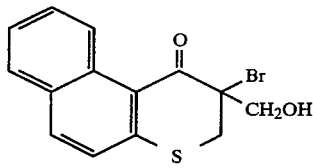

is reacted with a base to give the compound of Formula (II). Examples of the organic solvent to be used herein are tetrahydrofuran, dioxane, methanol, ethanol, isopropanol and N,N-dimethylformamide.

The compound of Formula (I) of the present invention can be formulated into the dosage form such as tablets, granules, capsules, powders, pills, injections, solutions and suppositories and administered orally, directly (e.g. intramascularly and intravenously) or rectally. The above dosage form can be prepared by using conventional fillers (e.g. crystalline cellulose, starch and lactic acid), binders (e.g. hydroxypropyl cellulose and polyvinylpyrrolidone) and lubricants (e.g. magnesium stearate and talc) according to a conventional manner (e.g. the method regulated in the Pharmacopoea of Japan, 12th Edition). The dose of the compound of Formula (I) depends on the condition, age and body weight of the patient, but usually the daily dose to adult may be from 0.5 mg to 50 mg, administration being effected once or several times depending on the condition.

BEST MODE OF CARRYING OUT THE INVENTION

The present invention is hereinafter illustrated in more detail by the following examples and experiment.

EXAMPLE 1

2-[(4-Methyl-1-imidazolyl)methyl]-1H-naphtho-[2,1-b]thiopyran-1-one (1) To a solution of 11.1 g of 2-bromo-2,3-dihydro-1H-naphtho[2,1-b]thiopyran-1-one in 300 ml of methanol were added 29 ml of 35% formalin and 5.74 g of potassium carbonate, and stirring was continued at 60° C. for 6 hours. After evaporation of the methanol under reduced pressure, the residue was dissolved in ethyl acetate, and the resulting solution was washed successively with 3N hydrochloric acid, water and a saturated aqueous sodium chloride solution, and dried over anhydrous sodium sulfate.

After evaporation of the solvent under reduced pressure, purification by silica gel column chromatography (eluant; n-hexane:ethyl acetate=5:1) and recrystallization from ethyl acetate - n-hexane gave 3.70 g of 2-hydroxymethyl-1H-naphtho[2,1-b]thiopyran-1-one.

m.p. 158°-159° C.

(2) To a solution of 1.49 g of the compound obtained in the item (1) in 20 ml of tetrahydrofuran and 1.6 ml of hexamethylphosphorus triamide was added dropwise 0.52 ml of thionyl chloride with stirring under ice-cooling. Stirring was further continued at room temperature for 3 hours, and the reaction solution, after addition of ice water, was extracted with ethyl acetate. The organic layer was washed successively with water, a saturated aqueous sodium bicarbonate solution, water and a saturated aqueous sodium chloride solution, and dried over anhydrous magnesium sulfate.

After evaporation of the solvent, the residue was recrystallized from dichloromethane - n-hexane to give 1.23 g of 2-chloromethyl-1H-naphtho[2,1-b]thiopyran-1-one.

m.p. 151°-153° C.

(3) To a solution of 0.30 g of the compound obtained in the item (2) and 0.10 g of 4-methylimidazole in 10 ml of N,N-dimethylformamide was added gradually 51 mg of sodium hydride (60% oil) under a nitrogen stream and ice cooling with stirring, and further stirring was continued for 20 minutes. The reaction solution, after addition of water, was extracted with ethyl acetate, and the organic layer was washed successively with water and a saturated aqueous sodium chloride solution and dried over anhydrous sodium sulfate.

After evaporation of the solvent under reduced pressure, the residue was purified by silica gel column chromatography (eluant; dichloromethane:methanol:35% ammonia water=90:10:0.5) and recrystallized from dichloromethane - n-hexane to give 66 mg of the title compound.

m.p. 180°-181° C.

EXAMPLE 2

2-Hydroxymethyl-1H-naphtho[2,1-b]thiopyran-1-one obtained in Example 1(1) was also prepared by another method as follows. (1) To a solution of 64.7 g of 2-bromo-2,3-dihydro-1H-naphtho [2,1-b]thiopyran-l-one in 200 ml of tetrahydrofuran were added 258 ml of 35% formalin and 32.2 g of potassium carbonate, and stirring was continued under ice cooling for 1.5 hours.

After evaporation of about 100 ml of the tetrahydrofuran under reduced pressure, water was added to the residue, and the resulting crystals were collected by filtration to give 64.3 g of 2-bromo-2- hydroxymethyl-2,3-dihydro-1H-naphtho[2,1-b]thiopyran- 1-one.

m.p. 85°-87° C.

(2) To a solution of 64.3 g of the compound obtained in the item (1) in 200 ml of tetrahydrofuran was added 29.3 g of triethylamine, and stirring was continued for 1.5 hours.

After evaporation of about 100 ml of the tetrahydrofuran under reduced pressure, water was added to the residue, and the resulting crystals were collected by filtration and recrystallized from dichloromethane - n-hexane to give 38.8 g of 2-hydroxymethyl-1H-naphtho[2,1-b]thiopyran-l-one.

m.p. 156°-158° C.

EXAMPLE 3

2-[(2-Methyl-1-imidazolyl)methyl]-1H-naphtho- [2,1-b]thiopyran-1-one

To a suspension of 0.17 g of sodium hydride in 10 ml of N,N-dimethylformamide was added 0.35 g of 2-methylimidazole under a nitrogen stream and ice cooling, and stirring was continued for 20 minutes. A solution of 1.0 g of the compound obtained in Example 1(2) in 20 ml of N,N-dimethylformamide was added under ice cooling, and stirring was continued for an hour. The reaction solution, after addition of water, was extracted with ethyl acetate, and the organic layer was washed successively with water and a saturated aqueous sodium chloride solution and dried over anhydrous sodium sulfate.

After evaporation of the solvent under reduced pressure, the residue was purified by silica gel column chromatography (eluant; dichloromethane:methanol:ammonia water=90:10:0.5) and recrystallized from dichloromethane - n-hexane to give 0.62 g of the title compound.

m.p. 212°-213° C. (decomposition).

EXAMPLE 4

2-[(2-Methyl-1-imidazolyl)methyl]-1H-naphtho-[2,1-b]thiopyran-1-one hydrochloride 0.1 g of 2-[(2-methyl-1-imidazolyl)methyl]- 1H-naphtho[2,1-b]thiopyran-1-one obtained in Example 3, after dissolving in methanol, was converted into the hydrochloride with conc. hydrochloric acid. After evaporation of the solvent under reduced pressure, the residue was recrystallized from methanol - diethyl ether to give 64 mg of the title compound.

m.p. 230° C. or above.

$^1$H-NMR (DMSO-d$_6$) δ ppm:
10.00(1H, m), 8.55(1H, s), 8.28(1H, d, J=8.5Hz), 8.11(1H, m), 7.92(1H, d, J=8.5Hz), 7.68-7.83(2H, m), 7.66(1H, d, J=2Hz), 7.58(1H, d, J=2Hz), 5.34(2H, s), 2.76(3H, s).

Experiment [Anti-vomiting Effect Test]

Emesis induced by cisplatin is known to be inhibited by antagonists at 5-HT$_3$ receptors. The anti-vomiting effect of the compound of the present invention was compared with that of the compound described in Example of Japanese Patent Kokai 2-209876 according to the method of Matsumoto et al [Japanese Journal of Pharmacology, vol. 48, pp. 303-306 (1988)].

Test samples

The compound obtained in Example 4 (hereinafter referred to as "Compound A") and the compound described in Example 1 of Japanese Patent Kokai 2-209876 (hereinafter referred to as "Compound B") were each suspended in 0.4% aqueous carboxymethylcellulose solution to give test samples.

Test method

Group each of six suncus of either sex weighing 40-60 g (male) and 30-50 g (female) were used. Each animal was placed with a chronic intravenous cannula 3 days before vomiting test. The samples prepared above were orally administered in the doses of 0.03-3 mg/kg to each group of the animals. After 45 minutes 30 mg/kg of cisplatin was administered intravenously, and number of emesises was determined for a period of 2 hours. Number of emesises for a period of 2 hours of a control group treated with 0.4% carboxymethylcellulose suspension alone was determined as well.

Test results

Number of emesises obtained above was expressed as compared with 100% of the control, and IC$_{50}$ value was calculated by number of emesises. Results are shown in Table 1.

TABLE 1

| Sample | Dose (mg/kg) | % value to control | IC$_{50}$ value (μg/kg) |
| --- | --- | --- | --- |
| Compound A | 0.03 | 77.8 | 90.4 |
|  | 0.3 | 17.0 |  |
|  | 3 | 4.4 |  |
| Compound B | 0.03 | 142.9 | 412.5 |
|  | 0.3 | 68.6 |  |
|  | 3 | 0.0 |  |

INDUSTRIAL UTILIZATION

The compounds of the present invention have the antagonist effect of serotonin at serotonin 3 recetors, and therefore are effective for the improvement and treatment of gastrointestinal dysfunctions (e.g. dyspepsia, peptic ulcer, gastritis, reflux esophagitis and irritable colon syndromes), symptoms accompanied by these dysfunctions, migraine and pain of trigemiral neuralgia. Particularly they are also effective for the treatment of nausea and vomiting caused by cancer chemotherapy and radiotherapy, arrhythmia and anxiety.

We claim:

1. A naphthothiopranone derivative represented by the formula:

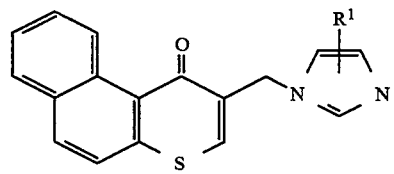

(wherein R$^1$ is a hydrogen atom or an alkyl group having 1 to 4 carbon atoms) or an acid addition salt thereof.

2. The naphthothiopyranone derivative as claimed in claim 1, wherein R$^1$ is a hydrogen atom.

3. The naphthothiopyranone derivative as claimed in claim 1, wherein R$^1$ is an alkyl group having 1 to 4 carbon atoms.

4. The naphthothiopyranone derivative as claimed in claim 1, wherein R$^1$ is a straight chain alkyl group having 1 to 4 carbon atoms.

5. The naphthothiopyranone derivative as claimed in claim 1, wherein R$^1$ is a branched chain alkyl group having 1 to 4 carbon atoms.

6. The naphthothiopyranone derivative as claimed in claim 1, represented by the formula

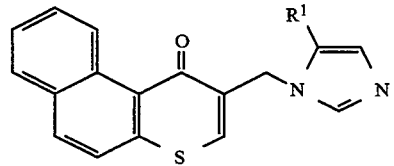

7. The naphthothiopyranone derivative as claimed in claim 6, wherein R$^1$ is a hydrogen atom.

8. The naphthothiopyranone derivative as claimed in claim 6, wherein R$^1$ is an alkyl group having 1 to 4 carbon atoms.

9. The naphthothiopyranone derivative as claimed in claim 6, wherein the naphthiopyranone derivative is the acid addition salt thereof.

10. The naphthothiopyranone derivative as claimed in claim 1, represented by the formula

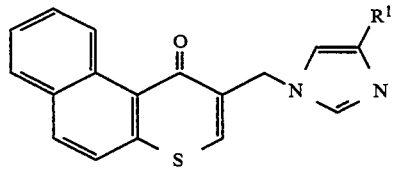

11. The naphthothiopyranone derivative as claimed in claim 10, wherein $R^1$ is a hydrogen atom.

12. The naphthothiopyranone derivative as claimed in claim 10, wherein $R^1$ is an alkyl group having 1 to 4 carbon atoms.

13. The naphthothiopyranone derivative as claimed in claim 10, wherein the naphthiopyranone derivative is the acid addition salt thereof.

14. The naphthothiopyranone derivative as claimed in claim 1, represented by the formula

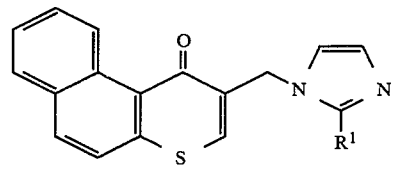

15. The naphthothiopyranone derivative as claimed in claim 14, wherein $R^1$ is a hydrogen atom.

16. The napthothiopyranone derivative as claimed in claim 14, wherein $R^1$ is an alkyl group having 1 to 4 carbon atoms.

17. The naphthothiopyranone derivative as claimed in claim 14, wherein the naphthiopyranone derivative is the acid addition salt thereof.

18. The naphthothiopyranone derivative as claimed in claim 1, wherein the naphthiopyranone derivative is the acid addition salt thereof, the acid being selected from the group consisting of hydrochloride, hydrobromide, hydroiodide, sulfate, acetate, citrate, maloate, maleate, tartarate and succinate.

* * * * *